US008262668B2

(12) United States Patent
Biegun

(10) Patent No.: US 8,262,668 B2
(45) Date of Patent: Sep. 11, 2012

(54) HIP FILE CARRIER WITH A MOVABLE JAW

(75) Inventor: Jean-François Biegun, Bavilliers (FR)

(73) Assignee: Xnov, Belfort (FR)

( * ) Notice: Subject to any disclaimer, the term of this patent is extended or adjusted under 35 U.S.C. 154(b) by 287 days.

(21) Appl. No.: 12/803,519

(22) Filed: Jun. 29, 2010

(65) Prior Publication Data

US 2010/0331902 A1    Dec. 30, 2010

(51) Int. Cl.
*A61B 17/60* (2006.01)
*A61B 17/58* (2006.01)
*A61F 2/00* (2006.01)

(52) U.S. Cl. .......................................................... 606/99

(58) Field of Classification Search .................... 606/79, 606/85, 86 R, 99
See application file for complete search history.

(56) References Cited

U.S. PATENT DOCUMENTS

| | | | |
|---|---|---|---|
| 4,306,550 A | 12/1981 | Forte | 128/92 |
| 4,583,270 A | 4/1986 | Kenna | 29/80 |
| 2003/0220698 A1 | 11/2003 | Mears et al. | 623/22.4 |
| 2007/0233134 A1 * | 10/2007 | Bastian et al. | 606/85 |

FOREIGN PATENT DOCUMENTS

| | | |
|---|---|---|
| DE | 39 35 518 | 5/1991 |
| FR | 2 627 983 | 9/1989 |

OTHER PUBLICATIONS

France International Search Report (2 pages, dated Jan. 15, 2010).

* cited by examiner

*Primary Examiner* — Kevin T Truong
*Assistant Examiner* — Sameh Boles
(74) *Attorney, Agent, or Firm* — Renner, Kenner, Greive, Bobak, Taylor & Weber

(57) ABSTRACT

File carrier which is intended to carry a file for filing bone of the medullary canal of the femur; a fixed jaw and a movable jaw are arranged at the distal end of the intermediate portion and there are provided means which are intended to control the movement of the movable jaw relative to the fixed jaw between a closed state in which the file is fixed in position on the file carrier and an open state in which the file is released from the file carrier; the position of the movable jaw in the open state is displaced in the mediolateral direction relative to the position of the movable jaw in the closed state.

17 Claims, 5 Drawing Sheets

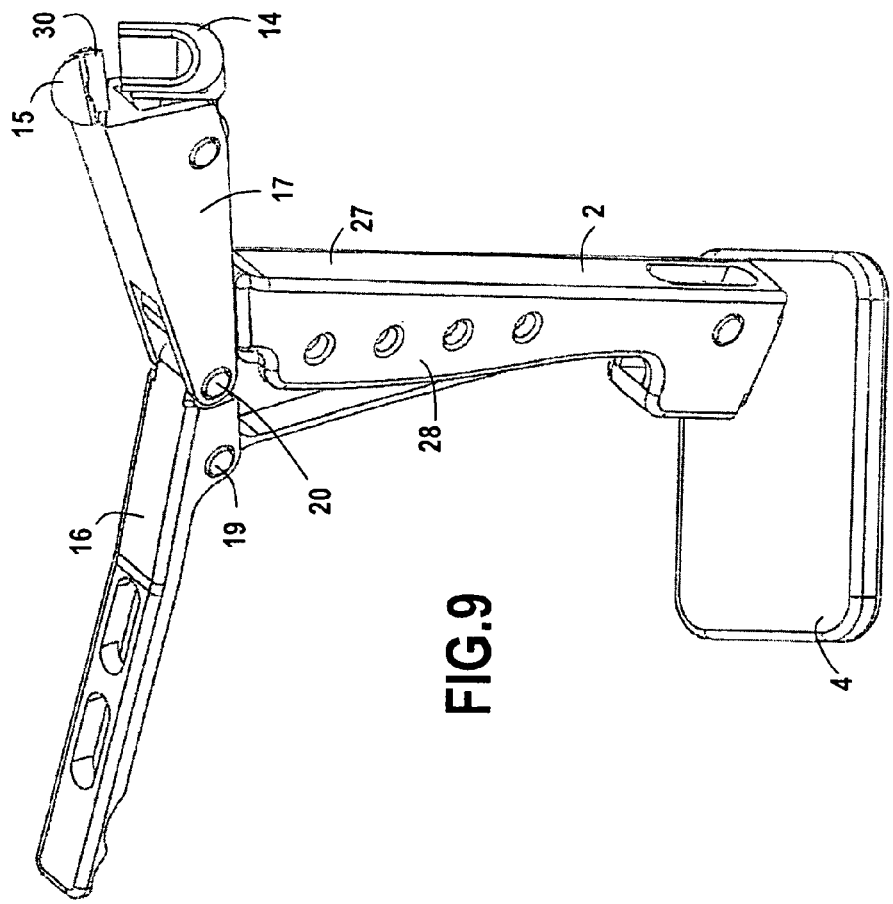
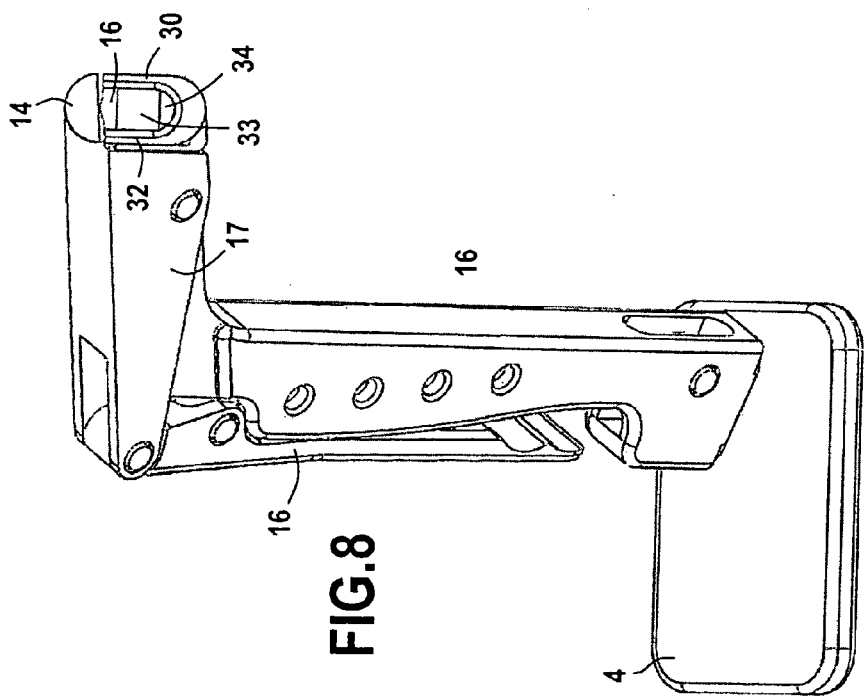

HIP FILE CARRIER WITH A MOVABLE JAW

The present invention relates to a file carrier which is intended to carry a file for filing bone of the medullary canal of the femur.

There are already known from the prior art file carriers which are constituted by a substantially sleeve-like member which comprises a proximal holding portion and an intermediate portion which extends along a longitudinal axis and which is inclined or which forms an angle with the longitudinal axis of the proximal portion, in particular an angle of approximately 135°, the distal end of the intermediate portion being intended to cooperate with a file, in particular a file which is substantially in the form of an anchoring brace of a hip prosthesis, that is to say, comprising portions in the form of indentations and having a neutral or medullary axis which extends through a plane of symmetry, as in a mirror, of the anchoring brace, the cooperation being such that the medullary axis is substantially parallel with the axis of the proximal portion and is displaced relative thereto so that the angle between the medullary axis and the longitudinal axis of the intermediate portion in the plane formed by those two axes is between 40° and 70° and is particularly of 55°.

According to the invention, a file carrier which is constituted by a substantially sleeve-like member and which comprises a proximal holding portion and an intermediate portion which extends along a longitudinal axis which is inclined or which forms an angle with the longitudinal axis of the proximal portion, in particular an angle of approximately 135°, the distal end of the intermediate portion being intended to retain a file which is substantially in the form of an anchoring brace of a hip prosthesis having a medullary axis, an anteroposterior axis and a mediolateral axis, the retention being such that the medullary axis is substantially parallel with the axis of the proximal portion and is displaced relative thereto so that the angle between the medullary axis and the longitudinal axis of the intermediate portion in the plane formed by those two axes is between 40° and 70° and is particularly of 55°;

wherein a fixed jaw and a movable jaw are arranged at the distal end of the intermediate portion and there are provided means which are intended to control the movement of the movable jaw relative to the fixed jaw between a closed state in which the file is fixed in position on the file carrier and an open state in which the file is released from the file carrier; and wherein the position of the movable jaw in the open state is displaced in the mediolateral direction relative to the position of the movable jaw in the closed state.

According to the invention, there is obtained a file carrier which is very simple to use, in particular in terms of positioning and withdrawing the file and which at the same time has a simple structure which takes up little space, particularly with regard to the space taken up by the means for controlling the clamping and unclamping of the file.

Use is particularly simple for the operator when he holds the file carrier particularly by means of an anvil-like member which is in the region of the proximal end of the proximal portion, in particular perpendicularly relative to the longitudinal axis of the portion, is also a very short distance from the control arm and can thereby readily operate in order to open and close the jaws and thereby to tighten or relax the anchoring brace or the file which is intended to be inserted in the medullary canal.

There will now be described, by way of example, a preferred embodiment of the invention with reference to the drawings, in which:

FIG. 8 is a side view of the file carrier of FIG. 7 in a direction perpendicular to the mediolateral and anteroposterior axes of the file when it is engaged in the jaws of the file carrier;

FIG. 9 is a side view of the file carrier of FIG. 6, in the same direction as in FIG. 8, perpendicular to the mediolateral and anteroposterior axes of the file when it is engaged in the jaws of the file carrier, that is to say that, in FIG. 9, the jaws are in the closed position whilst, in FIG. 8, they are in the open position;

Figure 1:
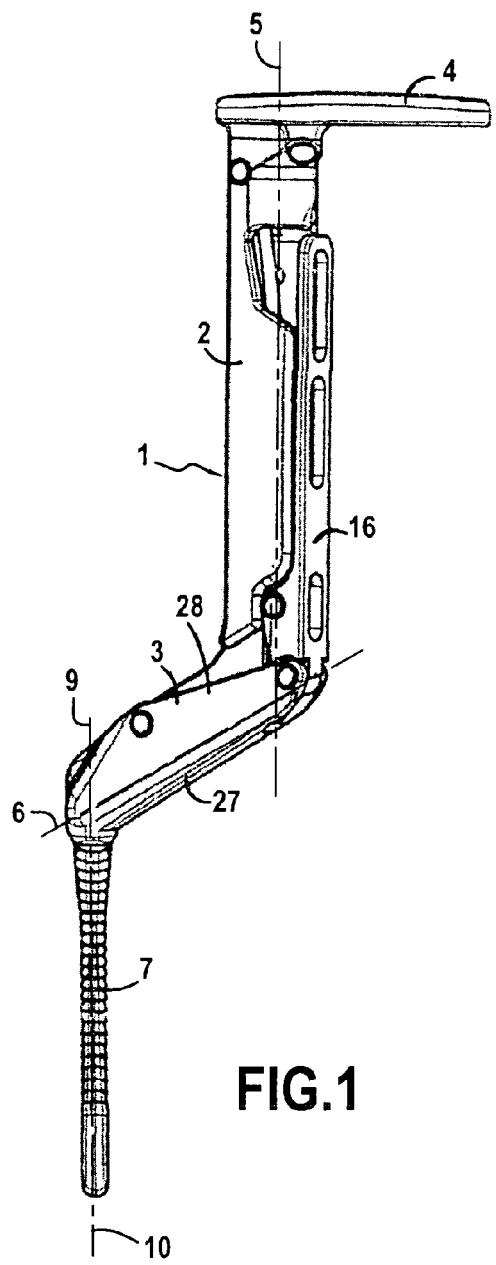
FIG. 1 is a side view, in a first direction, of a file carrier according to the invention, in which a file is carried.

The file carrier 1 is constituted by a proximal portion 2 and an intermediate portion 3. A rectangular proximal holding plate 4 is arranged at the proximal end of the proximal portion 2. The proximal holding plate or anvil-like member 4 is perpendicular to the axis of the proximal portion 2. The axis of the proximal portion 2 is referred to as the axis 5 of the file carrier. The intermediate portion also comprises a longitudinal axis 6, along which it extends. A file 7 is carried at the distal end of the file carrier 1 (that is to say, the distal end of the intermediate portion).

Figure 2:
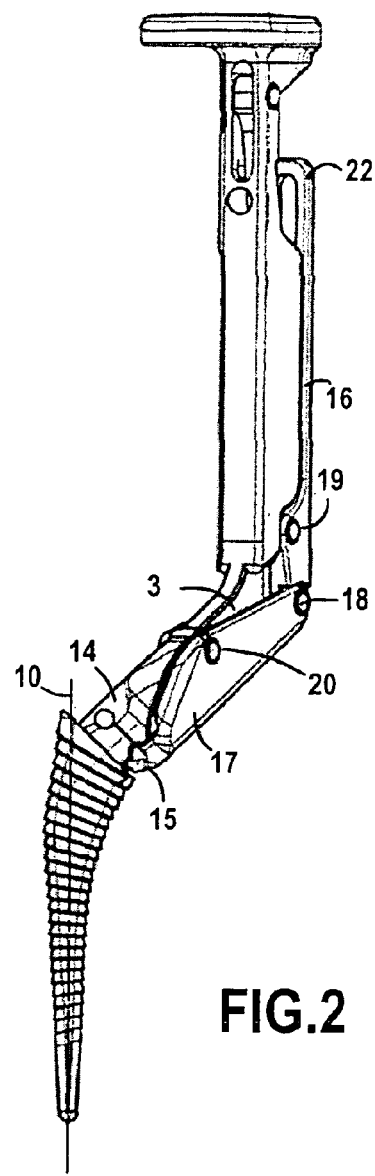
FIG. 2 is a side view in a second direction, perpendicular to the first direction, of the file carrier and the file of FIG. 1.

The file 7 is in the form of an anchoring brace of a femoral hip prosthesis, having a mediolateral axis (the direction that is horizontal relative to FIG. 1 and perpendicular relative to the plane of FIG. 2) and an anteroposterior axis (the direction that is horizontal relative to FIG. 2 and perpendicular relative to the plane of FIG. 1). It is intended to be introduced into the medullary canal of a femur in order to file the bone thereof in order to form therein a recess, in which a femoral hip prosthesis will then be inserted. The file has a tapered shape which is well known in the art. It is symmetrical, as in a mirror, relative to a plane 9 of symmetry which is parallel with the plane of FIG. 2 and which is illustrated in FIG. 1, the plane 9 being perpendicular to the plane of FIG. 1. The medullary axis 10, also referred to as the neutral axis of the prosthesis, extends through the plane 9.

At the proximal end, that is to say, opposite the tip of the anchoring brace or femoral shaft, the femoral shaft comprises a stud 12 which is particularly of cylindrical shape and in which there are formed two diametrically opposed recesses 13 which have a substantially semi-circular cross-section.

In the plane in which the two axes 5 and 6 are located, the angle between those two axes is 135°. At the distal end which is intended to cooperate with the stud 12 of the femoral shaft, the intermediate portion 3 comprises a fixed jaw 14 and a movable jaw 15. The movable jaw 15 comprises a lateral end portion which forms a rib 30 which is of semi-circular cylindrical shape corresponding to the recesses 13 of the stud 12.

Figure 3:
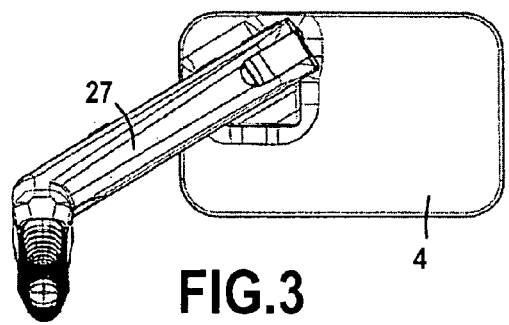
FIG. 3 is a bottom view of the file carrier and the file of FIGS. 1 and 2.
Figure 4:
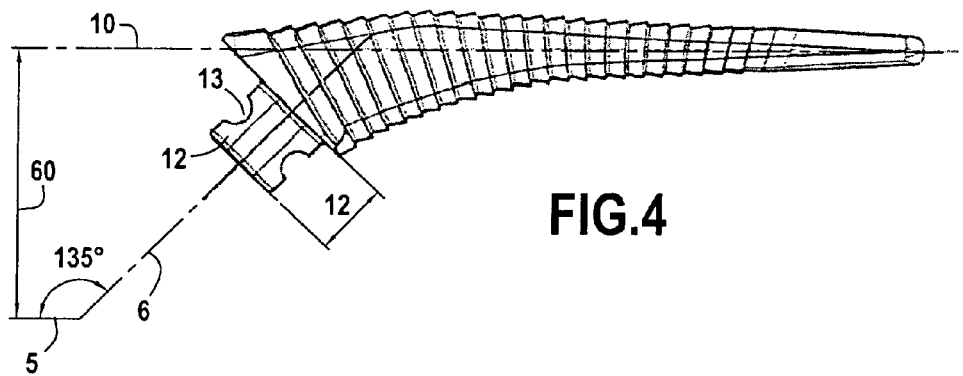
FIG. 4 is an illustration showing only the file relative to lines representing the longitudinal axes of the proximal and intermediate portions of the file carrier in the plane of FIG. 1.
Figure 5:
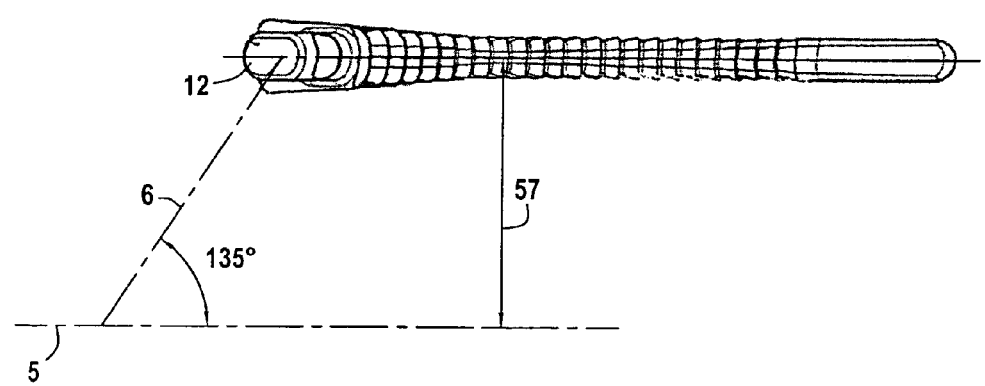
FIG. 5 is an illustration of the same type as that in FIG. 4 but in the plane perpendicular to the plane of FIG. 4 and corresponding to the plane of FIG. 2.
Figure 7:
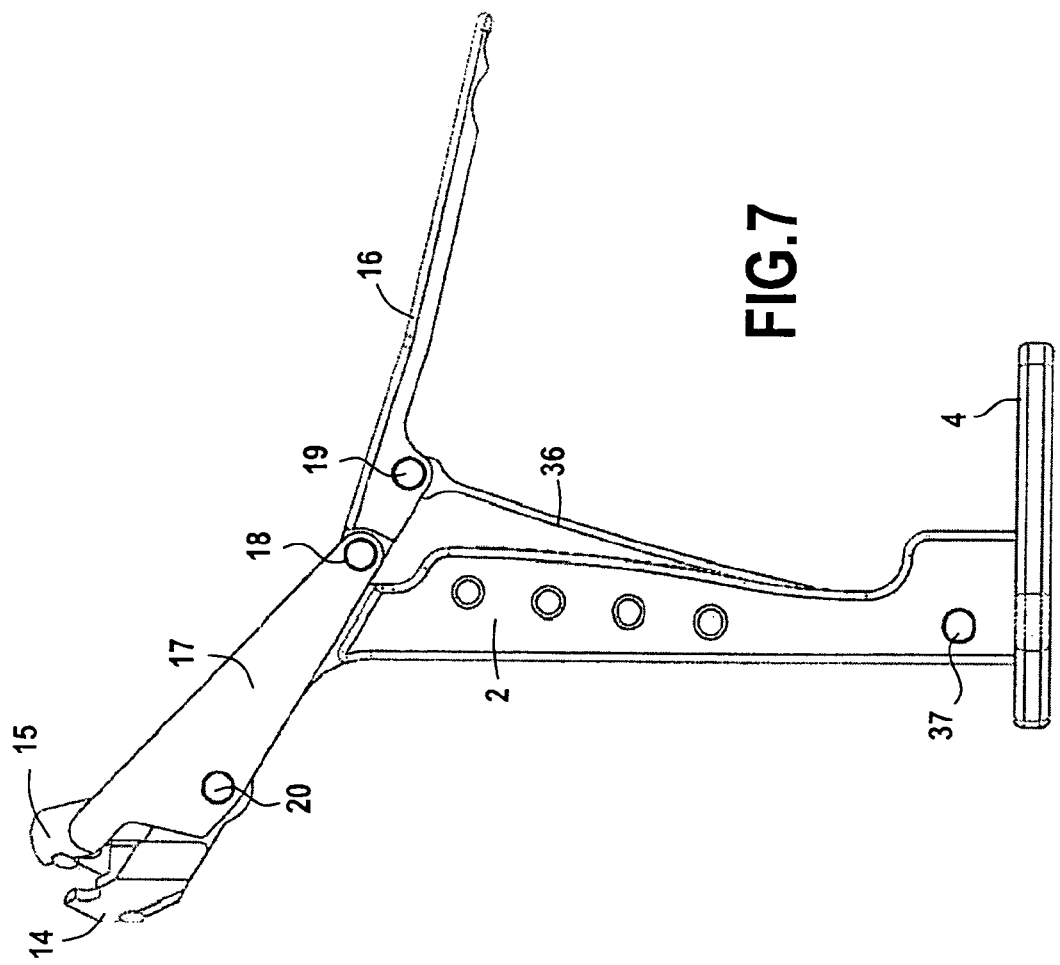
FIG. 7 is a side view, in the same direction perpendicular to the longitudinal axis of the proximal portion as in FIG. 6, of the file carrier of FIG. 1, without the file and with the fixed and movable jaws in the open position, that is to say, the position in which the file could, if it were present between the jaws, be withdrawn from the file carrier.
Figure 6:
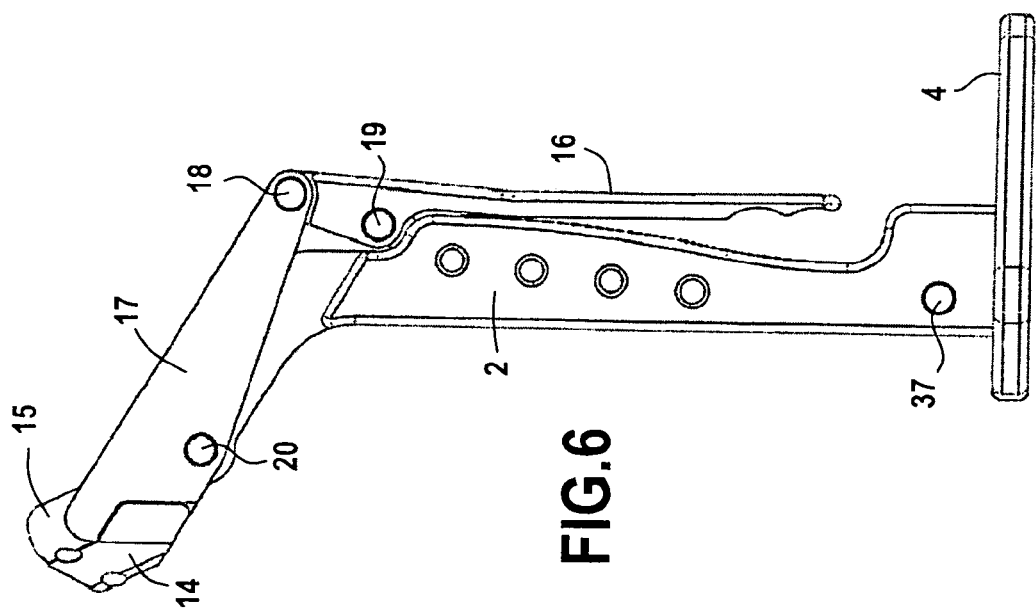
FIG. 6 is a side view, in the direction perpendicular to the longitudinal axis of the proximal portion, of the file carrier of FIG. 1, without the file and with the fixed and movable jaws in the closed position, that is to say, the position in which the file carrier would secure the file if it were present.
Figure 10:
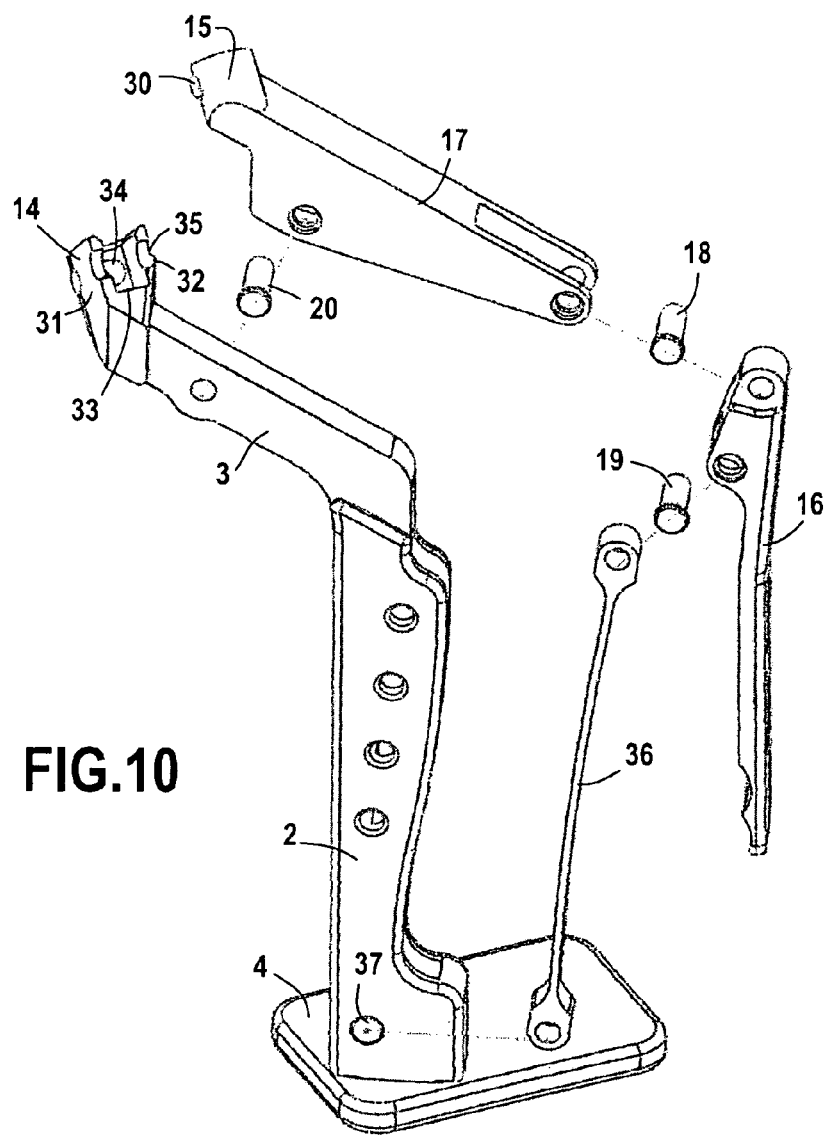
FIG. 10 shows the various elements which constitute the file carrier and which have been separated from each other in order to allow complete understanding of the structure thereof.
Figure 11:
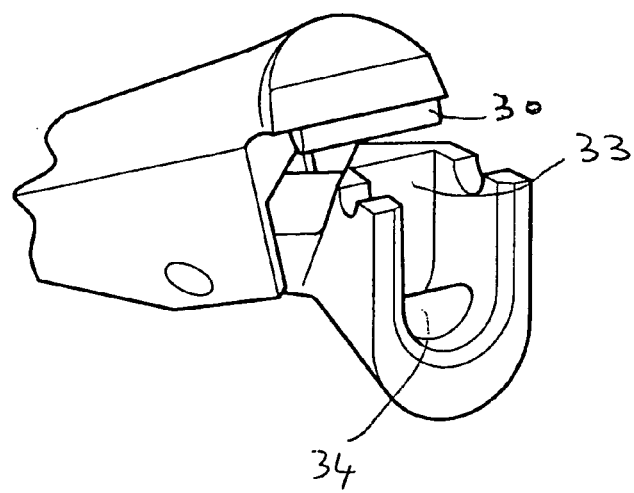
FIG. 11 is a perspective view, showing greater detail, of the two fixed and movable jaws in the open position, that is to say, remote from each other.

As can clearly be seen in FIG. 11, the fixed jaw 14 defines a recess which is for receiving the stud 12 and which is open at the side of the free jaw 15 and at the distal side, via which the file will be introduced. In this manner, the receiving recess comprises two connected parallel side walls 31 and 32 which are joined together in a U-like manner. Furthermore, at the side opposite the distal opening (through which the file passes when it is engaged in the jaws as illustrated in the FIGS. 1 to 3), there is a base wall 33 which is perpendicular to the two side walls 31 and 32. In this manner, the walls 31, 32 and 33 define a space which has a shape corresponding to the stud 12. At the bottom of the U, between the two walls 31 and 32 and perpendicularly thereto, there is formed a rib 34 of semi-circular cylindrical shape corresponding to the recesses 13 of the stud 12. The upper edges of the two side walls 31 and 32 each comprise a semi-circular cutout 35 which is intended to receive the ends of the rib 30 of the movable jaw when it is closed on the fixed jaw.

When the two jaws are clamped against each other, the two ribs 30 and 34 are introduced into the recesses 13 in order to secure the stud 12 and therefore the file and to fix the femoral shaft securely to the file carrier.

The movement of the movable jaw 15 relative to the fixed jaw 14 is controlled by means of a first proximal arm 16 and a second distal arm 17. The proximal arm 16, in the closed position of the jaws, extends along the proximal portion 2 whilst the second distal arm 17 extends along the intermediate portion 3. The two arms 16 and 17 are articulated to each other by an articulation axle 18 which is substantially at the distal end of the proximal portion 2 and substantially at the proximal end of the intermediate portion 3, that is to say, substantially in the region where the two portions become joined.

The proximal arm 16 is further mounted so as to be articulated via an axle 19 to the distal end of a resilient plate 36 which is mounted so as to be rotatable at the proximal end thereof at an axle 37 at the proximal end of the proximal portion 2, the axle 37 being fixedly joined to the proximal portion. The second distal arm 17 is mounted so as to be rotatable relative to the intermediate portion 3 relative to an axis 20 of rotation which is parallel with the axles 18, 19 and 37 and which is on the intermediate portion.

The axis 20 of rotation is substantially half-way between the articulation axle 18 and the end forming the jaws of the intermediate portion.

The axle 19 is near the articulation axle 18 (and parallel therewith), the distance between the two axles 18 and 19 substantially corresponding to the thickness (transverse dimension relative to the longitudinal axis 6 thereof) of the intermediate portion. The axle 19 is more proximal than the axle 18, that is to say, is nearer the anvil-like member 4 or the operator.

The proximal and intermediate portions are each substantially in the form of a tube having a square or rectangular cross-section which is open at one side. The arm 16 is in the form of a rectangular planar rod and, in the closed position of the jaws, extends along the proximal portion so as to close the opening of the tube at least partially. Similarly, the arm 17 is constituted by a thin base plate 27 and two thin plates 28 which form a rim which extends perpendicularly relative to the base plate 27, the two rim-forming plates receiving in a sandwich-like manner the open tube which forms the intermediate portion so as to close at least partially the open side of the intermediate portion. In the plane formed by the two longitudinal axes 5 and 6 of the two proximal and intermediate portions, the arm 16 is at the side of the proximal portion which is opposite the intermediate portion. Similarly, the arm 17 is at the side of the intermediate portion which is opposite the proximal portion. In this manner, when the proximal portion is viewed in the axis of the intermediate portion from a position at the side of the intermediate portion, it is substantially impossible to see the arm 16, the arm being hidden by the proximal portion. Similarly, when the intermediate portion is viewed in the axis of the proximal portion from a position at the side of the proximal portion, it is substantially impossible to see the arm 17, and in particular the plate 27, which is hidden by the intermediate portion.

In order to insert the file, the user has to move the jaws apart from each other. To do this, he pivots the arm 16 and moves it away from the proximal portion 2. The rotation of the arm 16, owing to the articulation 20, rotates in the opposite direction the arm 17, to which the movable jaw 15 is fixedly joined at the distal end thereof and thereby moves away from the fixed jaw 14 in order either to release the file if it is at that location or to allow insertion thereof in the recess defined by the walls 31, 32 and 33.

When the jaw 15 moves away from the jaw 14 in order to move into an open position, the movable jaw 15 moves along a trajectory which not only has a component in the anteroposterior direction of the brace or file but also has a component in the mediolateral direction, as can be seen very clearly in FIG. 8, in which it can be seen that the jaw has moved upwards (anteroposterior direction) and to the left (therefore, mediolaterally) in relation to FIG. 9.

The proximal portion comprises, in its proximal portion in the region of the proximal plate (the anvil-like member), a recess 21. The proximal arm 16 extends in such a manner that the proximal end 22 thereof is in the region of the recess 21 in order to facilitate the handling of the arm 16, the user readily being able to introduce his finger into the recess 21 between the proximal portion 2 and the arm 16 in order subsequently to pivot the arm 16 outwards. In the position illustrated in the Figures, the arm 16 is in a position against the proximal portion, the jaws 14 and 15 being clamped against each other so as to lock the stud 12 between them by cooperation of the rib-like portion 30, 34 thereof in the recesses 13 of the stud 12. When the operator moves the arm 16 away from the proximal portion, the distal end of the arm 16 is subjected to a rotational movement in relation to the axle 19, which has the effect of pivoting the arm 17 in a clockwise direction in FIG. 1 relative to the axle 20 and moving the movable jaw 15 away from the stud 12 in order to release it.

When the arm 16 is moved away by the proximal portion being pivoted in order to open the jaws, it also rotates the resilient plate 36 relative to the axle 37. In this manner, the plate relaxes in terms of tension and moves away from the proximal portion 2. When the jaws are closed, the arm 16 is moved against the proximal portion in a manner parallel therewith and the plate 36 is also moved inside the portion 2 and is tensioned. That compression fixes, by means of resilient force, the arm 16 against the proximal portion and prevents inadvertent movement of the arm 16 away from the portion 2, and therefore inadvertent opening of the jaws. When the user wishes to open the jaws and moves the arm 16 away in a pivoting manner, he must thus act with a given force in order to overcome the return force of the resilient plate.

The medullary axis of the femoral shaft and the axis of the file carrier are parallel. The proximal plate or anvil-like member is perpendicular to the axis of the file carrier, the femoral shaft comprising a resection plane 25 which is the plane perpendicular to the axis of the stud 12.

The anvil-like member 4 is connected to the proximal portion by its upper right zone for a file carrier for the right-hand side.

The Figures illustrate a file carrier for the right-hand side. For a file carrier for the left-hand side, the anvil-like member would be connected to the member by the upper left location thereof.

The invention claimed is:

1. File carrier which is constituted by a substantially sleeve-like member and which comprises a proximal holding portion and an intermediate portion which extends along a longitudinal axis which is inclined or which forms an angle with the longitudinal axis of the proximal portion, the distal end of the intermediate portion being intended to retain a file which is substantially in the form of an anchoring brace of a hip prosthesis having a medullary axis, an anteroposterior axis and a mediolateral axis, the retention being such that the medullary axis is substantially parallel with the axis of the proximal portion and is displaced relative thereto so that the angle between the medullary axis and the longitudinal axis of the intermediate portion in the plane formed by those two axes is between 40° and 70°; wherein a fixed jaw and a pivotable jaw are arranged at the distal end of the intermediate portion; means for controlling the movement of the pivotable jaw relative to the fixed jaw between a closed state in which the file is fixed in position on the file carrier and an open state in which the file is released from the file carrier; and wherein the position of the pivotable jaw in the open state is displaced in the mediolateral direction relative to the position of the pivotable jaw in the closed state.

2. File carrier according to claim 1, characterised in that the movement control means of the pivotable jaw comprise a first proximal arm and a second distal arm, the first proximal arm being mounted so as to be rotatable relative to a first proximal axis, which is perpendicular to the longitudinal axis of the proximal portion and the longitudinal axis of the intermediate portion, the first proximal arm being mounted so as to be articulated to the second distal arm at a second axis which is parallel with the first proximal axis and the second distal arm is mounted so as to be rotatable relative to the intermediate portion relative to a third distal axis, which is fixedly joined to the intermediate portion, the second axis being more distal than the first axis and less distal than the third axis, and the pivotable jaw is fixedly joined to the second arm.

3. File carrier according to claim 2, characterised in that the distal end of the first proximal arm is mounted so as to be articulated to the proximal end of the second distal arm.

4. File carrier according to claim 2, characterised in that the third distal axis is parallel with the first and second axes.

5. File carrier according to claim 2, characterised in that there is further provided a resilient plate which acts counter to the pivoting of the first arm towards the outer side of the proximal portion.

6. File carrier according to claim 5, characterised in that the resilient plate is mounted so as to be rotatable relative to the first portion and is articulated to the first arm.

7. File carrier according to claim 2, characterised in that, in the plane formed by the two longitudinal axes (5) and (6) of the two proximal and intermediate portions, the arm (16) is at the side of the proximal portion which is opposite the intermediate portion in such a manner that, when the proximal portion is viewed in the axis of the intermediate portion from a position at the side of the intermediate portion, it is substantially impossible to see the arm (16), the arm being hidden by the proximal portion.

8. File carrier according to claim 7, characterised in that the arm (17) is at the side of the intermediate portion which is opposite the proximal portion in such a manner that, when the intermediate portion is viewed in the axis of the proximal portion from a position at the side of the proximal portion, it is substantially impossible to see the arm (17), and in particular the plate (27), which is hidden by the intermediate portion.

9. File carrier according to claim 1, characterised in that the position in the open state of the pivotable jaw is also displaced relative to the position thereof in the closed state in the anteroposterior direction.

10. File carrier according to claim 1, characterised in that at least one of the jaws comprises at least one rib which is intended to be introduced into a corresponding recess which is formed in the file when it is secured between the jaws.

11. File carrier according to claim 10, characterised in that the at least one rib is of semi-circular cylindrical shape.

12. File carrier according to claim 10, characterised in that each jaw of the fixed and pivotable jaws comprises a rib which is intended to be introduced into a recess of the file when the file is secured between the jaws.

13. File carrier according to claim 1, characterised in that a file is secured between the jaws.

14. File carrier according to claim 13, characterised in that each jaw of the fixed and pivotable jaws comprises a rib in a recess of the file which is secured between the jaws.

15. File carrier according to claim 1, characterised in that the intermediate portion is inclined or forms an angle with the longitudinal axis of the proximal portion of approximately 135°.

16. File carrier according to claim 15, characterised in that the angle between the medullary axis and the longitudinal axis of the intermediate portion in the plane formed by those two axes is of 55°.

17. File carrier according to claim 1, characterised in that the angle between the medullary axis and the longitudinal axis of the intermediate portion in the plane formed by those two axes is of 55°.

\* \* \* \* \*